United States Patent [19]

Kawamura et al.

[11] Patent Number: 5,279,303
[45] Date of Patent: Jan. 18, 1994

[54] BLOOD PRESSURE MONITOR SYSTEM

[75] Inventors: Norio Kawamura, Nagoya; Tsuneo Nakagawa, Kani; Ye Aung, Komaki, all of Japan

[73] Assignee: Colin Electronics Co., Ltd., Aichi, Japan

[21] Appl. No.: 894,515

[22] Filed: Jun. 4, 1992

[30] Foreign Application Priority Data

Jun. 14, 1991 [JP] Japan .................. 3-170497

[51] Int. Cl.⁵ .............................................. A61B 5/04
[52] U.S. Cl. ................................................ 128/683
[58] Field of Search ........ 128/677-683, 687-690, 672

[56] References Cited

U.S. PATENT DOCUMENTS 4,928,701  5/1990  Harada et al. ................ 128/681

FOREIGN PATENT DOCUMENTS 0152848  8/1985  European Pat. Off. .
0334652  9/1989  European Pat. Off. .
2605528  8/1977  Fed. Rep. of Germany .
3606602  9/1986  Fed. Rep. of Germany .
1-161707  11/1989  Japan .
8803003  5/1988  PCT Int'l Appl. .
WO88/04910  7/1988  PCT Int'l Appl. .

*Primary Examiner*—William E. Kamm
*Assistant Examiner*—Marianne Parker
*Attorney, Agent, or Firm*—Oliff & Berridge

[57] ABSTRACT

A blood pressure monitor system, including a pulse wave detecting device detecting a pulse wave produced from an artery of a living subject, a blood pressure measuring device including a pressing device, for measuring a blood pressure of the subject by pressing a body portion of the subject with the pressing device, a relationship determining device determining a relationship between blood pressure and pulse wave magnitude, based on a pulse wave magnitude detected by the pulse wave detecting device and a blood pressure value measured by the blood pressure measuring device, a blood pressure monitor device continuously determining, according to the relationship, blood pressure values of the subject based on magnitudes of the pulse wave detected by the pulse wave detecting device, the relationship determining device updating the relationship at intervals of time, based on blood pressure values measured by the blood pressure measuring device, a blood pressure variation determining device determining a variation of the blood pressure of the subject, based on at least two of the magnitudes of the pulse wave detected by the pulse wave detecting device, and an update-interval changing device changing the interval of updating based on the blood pressure variation determined by the blood pressure variation determining device.

22 Claims, 7 Drawing Sheets

BLOOD PRESSURE MONITOR SYSTEM

BACKGROUND OF THE INVENTION

Field of the Invention

The present invention generally relates to a blood pressure monitor system and in particular to such a monitor system which continuously determines blood pressure values of a living subject, according to a predetermined relationship between blood pressure and pulse wave magnitude, based on detected magnitudes of a pulse wave.

Related Art Statement

There is known a blood pressure monitor apparatus of the type which includes (a) a pulse wave detecting device detecting a pulse wave produced from an artery of a living subject, (b) a blood pressure measuring device measuring a blood pressure of the subject by pressing the subject's body portion with a pressing device, (c) a relationship determining means determining a relationship between blood pressure and pulse wave magnitude, based on a pulse wave magnitude detected by the pulse wave detecting device and a blood pressure value measured by the blood pressure measuring device, and (d) a blood pressure monitor means continuously determining, according to the determined relationship, blood pressure values of the subject based on magnitudes of the pulse wave detected by the pulse wave detecting device, and in which apparatus the relationship determining means updates the relationship at predetermined regular intervals of time, based on blood pressure values measured by the blood pressure measuring device. An example of the monitor system is disclosed in a Japanese Patent Application filed by the Assignee of the present application, which was laid open under Publication No. 1(1989)161707. The monitor system is used for, for example, monitoring the blood pressure of a patient after, or during, a surgical operation.

For sufficiently accurately monitoring the blood pressure of the patient based on the pulse wave detected by the pulse wave detecting device, it is desirable to update as frequently as possible the relationship between blood pressure and pulse wave magnitude (hereinafter, referred to as the "BP-PW relationship"). However, for updating of the BP-PW relationship, the blood pressure measuring device is required to measure an actual or standard blood pressure of the patient, which in turn involves the pressing of his or her body portion (e.g., upper arm) with the pressing device (e.g., inflatable cuff). If the BP-PW relationship is updated so frequently, however, the patient feels discomfort each time due to the pressing of the upper arm. Thus, the requirement that the blood pressure monitoring be effected with accuracy is not compatible with the requirement that patient's discomfort be reduced. In the conventional blood pressure monitor apparatus, the interval of updating of the BP-PW relationship is selected, as a compromise between the above two requirements, at a time duration (e.g., 5 to 10 minutes) which is not too long and not too short. However, if the patient's blood pressure varies largely in a very short time, the BP-PW relationship tends to be inappropriate or inaccurate, thereby lowering the accuracy of the blood pressure monitor based on the pulse wave detected by the pulse wave detecting device.

SUMMARY OF THE INVENTION

It is therefore an object of the present invention to provide a blood pressure monitoring system which continuously determines blood pressure values of a living subject, according to a relationship between blood pressure and pulse wave magnitude, based on actually detected magnitudes of a pulse wave, and updates the relationship at intervals of time based on blood pressure values actually measured using a pressing device, which system reduces patient's discomfort due to the unnecessarily frequent pressing with the pressing device when the patient's blood pressure does not vary so largely and provides accurate blood pressure monitoring when the blood pressure varies largely.

The above object has been achieved by the present invention, which provides a blood pressure monitoring system, comprising (a) pulse wave detecting means for detecting a pulse wave produced from an artery of a living subject, (b) blood pressure measuring means including a pressing device, for measuring a blood pressure of the subject by pressing a body portion of the subject with the pressing device, (c) relationship determining means for determining a relationship between blood pressure and pulse wave magnitude, based on a pulse wave magnitude detected by the pulse wave detecting means and a blood pressure value measured by the blood pressure measuring means, (d) blood pressure monitoring means for continuously determining according to the relationship, blood pressure values of the subject based on magnitudes of the pulse wave detected by the pulse wave detecting means, the relationship determining means updating the relationship at intervals of time, based on blood pressure values measured by the blood pressure measuring means, (e) blood pressure variation determining means for determining a variation of the blood pressure of the subject, based on at least two of the magnitudes of the pulse wave detected by the pulse wave detecting means, and update-interval changing means for changing the interval of updating based on the blood pressure variation determined by the blood pressure variation determining means.

In the blood pressure monitoring system constructed as described above, the relationship determining means determines a relationship between blood pressure and pulse wave magnitude, based on a pulse wave magnitude detected by the pulse wave detecting means and a blood pressure value measured by the blood pressure measuring means, and the blood pressure monitoring means continuously determines or estimates, according to the relationship, blood pressure values of the subject based on respective magnitudes of the pulse wave detected by the pulse wave detecting means. The relationship determining means updates the relationship at intervals of time, based on standard blood pressure values actually measured by the blood pressure measuring means. The present monitor system further includes blood pressure variation determining means for determining a variation of the blood pressure of the subject, based on at least two of the above-indicated respective magnitudes of the pulse wave, and update-interval changing means for changing the interval of updating based on the blood pressure variation determined by the blood pressure variation determining means. For example, when the variation of the blood pressure is sufficiently small and therefore the detected pulse wave is stable, the present system lengthens the interval of updating and consequently the interval of the blood pressure measurement using the pressing device. Thus, the present system advantageously reduces patient's discomfort due to otherwise more frequent pressing of his or her body portion with the pressing device. Meanwhile, when the blood pressure variation is excessively large, the present system shortens the interval of updating, for determining an appropriate relationship to provide accurate blood pressure monitoring based on the pulse wave detected by the pulse wave detecting means.

According to a preferred feature of the present invention, the blood pressure variation determining means determines (a) as a first variation of the blood pressure of the subject an absolute value of a difference between a maximum magnitude of each of pulses of the pulse wave detected by the pulse wave detecting means and a maximum magnitude of another of the pulses detected a first predetermined time before the each pulse, determines (b) as a second variation of the blood pressure an absolute value of a difference between the maximum magnitude of the each pulse and a maximum magnitude of yet another of the pulses detected a second predetermined time before the each pulse, the second predetermined time duration being shorter than the first predetermined time duration, determines (c) as a third variation of the blood pressure an absolute value of a difference between an amplitude of the each pulse and an amplitude of the another pulse, and determines (d) as a fourth variation of the blood pressure an absolute value of a difference between the amplitude of the each pulse and an amplitude of the yet another pulse, the update-interval changing means changing the interval of updating, by commanding the blood pressure measuring means and the relationship determining means to update the relationship, when the first, second, third, and fourth variations of the blood pressure are greater than a first and a second predetermined reference value and a third and a fourth reference value, respectively, the update-interval changing means determining the third reference value based on the amplitude of the another pulse, and the fourth reference value based on the amplitude of the yet another pulse.

According to another feature of the present invention, the blood pressure variation determining means selects, from pulses of the pulse wave detected by the pulse wave detecting means during a first predetermined time duration after the relationship is updated by the relationship determining means, a pulse having a greatest maximum magnitude, MAX, of maximum magnitudes of the pulses and a pulse having a smallest minimum magnitude, MIN, of minimum magnitudes of the pulses, calculates an average, MID, of the magnitudes MAX, MIN, calculates an average, AV, of the maximum and minimum magnitudes of the pulses except the magnitudes MAX, MIN, determines as a deviation, D, an absolute value of a difference between the averages MID, AV, and successively calculates an average, AV', of maximum and minimum magnitudes of pulses of the pulse wave detected during every second predetermined time duration after the deviation D is determined, the blood pressure variation determining means determining, as the variation of the blood pressure of the subject, an absolute value of a difference between time-wise adjacent two out of the average AV and the averages AV'. In this case, the update-interval changing means may change the interval of updating, by commanding the blood pressure measuring means and the relationship determining means to update the relationship, when the variation of the blood pressure is greater than the deviation D.

According to yet another feature of the present invention, the blood pressure variation determining means selects, from pulses of the pulse wave detected by the pulse wave detecting means during a predetermined time duration after the relationship is updated by the relationship determining means, a pulse having a greatest maximum magnitude of maximum magnitudes of the pulses and a pulse having a smallest maximum magnitude of the maximum magnitudes, and determines, as the variation of the blood pressure of the subject, an absolute value of a difference between the greatest and smallest maximum magnitudes. In this case, the update-interval changing means may determine a first weighted value, a, corresponding to the variation of the blood pressure, and a second weighted value, b, corresponding to a value of a physiological indicator indicative of a physical condition of the subject different from the maximum magnitude of the pulses of the pulse wave, and changes the interval of updating based on the weighted values a, b. The update-interval changing means may change the interval of updating to a value obtained by dividing a reference value by a sum of the weighted values a, b.

According to a further feature of the present invention, the blood pressure variation determining means determines the variation of the blood pressure of the subject, by utilizing at least one physiological indicator selected from maximum magnitude, minimum magnitude, average magnitude, and amplitude of the pulses of the pulse wave detected by the pulse wave detecting means.

According to another feature of the present invention, the monitor system further comprises display means for displaying a waveform of the pulse wave detected by the pulse wave detecting means, the blood pressure value measured by the blood pressure measuring means, and the blood pressure values determined by the blood pressure monitoring means.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
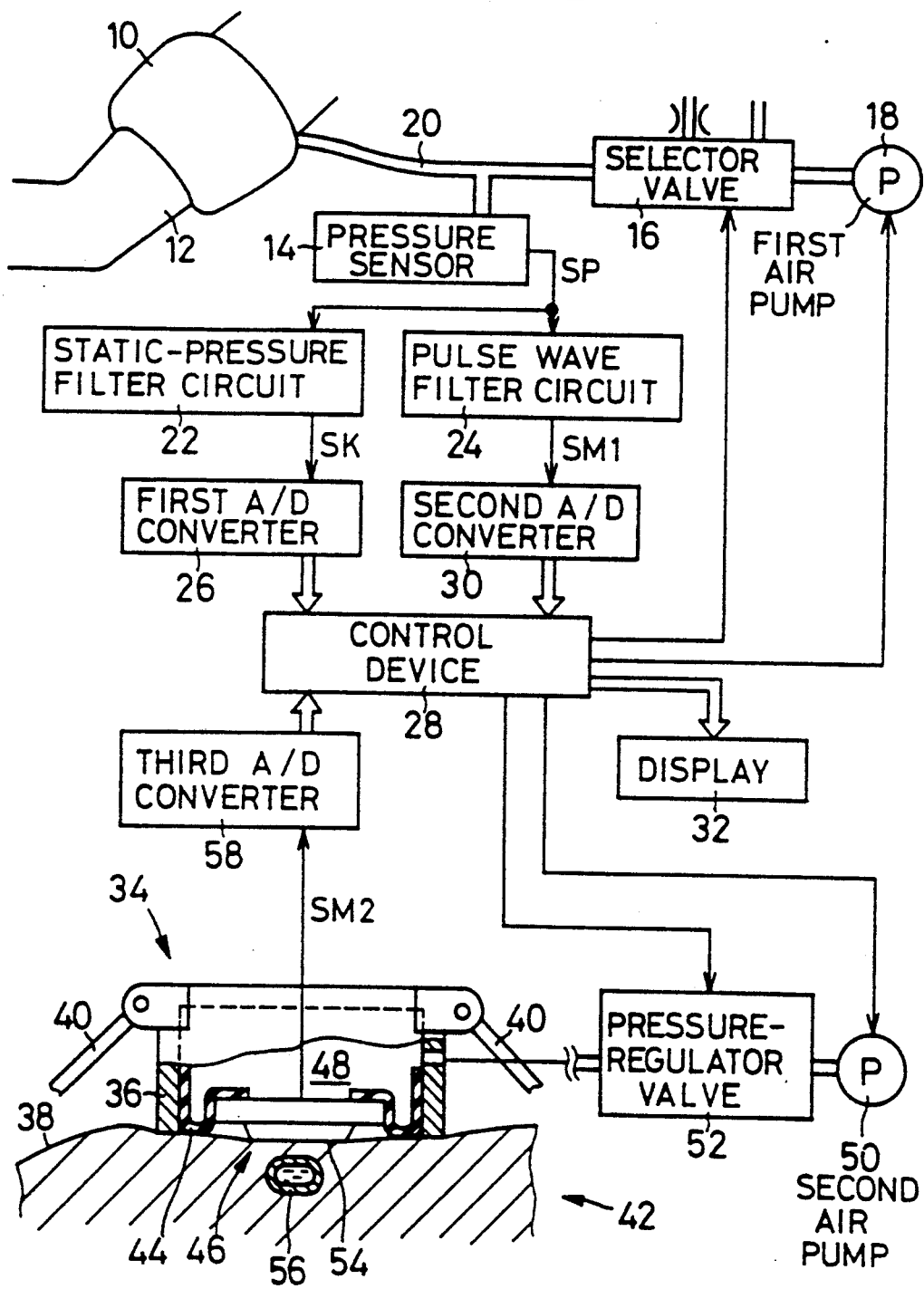
FIG. 1 is a diagrammatic view of a blood pressure monitor system embodying the present invention.

Referring first to FIG. 1, there is shown a blood pressure monitoring system embodying the present invention. The present monitor system is used for, for example, monitoring the physical condition of a patient during, or after, a surgical operation. In the figure, reference numeral 10 designates a bag-like, inflatable cuff formed of rubber. The cuff 10 is worn on the patient by being wound around, for example, an upper arm 12 of the patient. A pressure sensor 14, a selector valve 16, and a first air pump 18 are connected to the cuff 10 via piping 20.

The selector valve 16 is selectively placed in an INFLATION position, a SLOW-DEFLATION position, and a QUICK-DEFLATION position. In the INFLATION position, the selector valve 16 permits pressurized air to be supplied from the first air pump 18 to the cuff 10; in the SLOW-DEFLATION position, the valve 16 permits the pressurized air to slowly be discharged from the cuff 10 to atmosphere; and in the QUICK-DEFLATION position, the valve 16 permits the pressurized air to quickly be discharged from the cuff 10 to atmosphere.

The pressure sensor 14 detects the air pressure in the cuff 10, and supplies an electric signal, SP, representative of the detected pressure, to a static-pressure filter circuit 22 and a pulse-wave filter circuit 24. The static-pressure filter circuit 22 includes a low-pass filter and transmits, as a cuff-pressure signal SK, a static ("DC") component of the signal SP. The cuff pressure signal SK is representative of a static pressure, P, of the cuff 10 (hereinafter, referred to simply as the "cuff pressure P"). The cuff pressure signal SK is supplied to a control device 28 via a first analog to digital (A/D) converter 26.

Meanwhile, the pulse-wave filter circuit 24 includes a band-pass filter and transmits, as a pulse-wave signal $SM_1$, an oscillating ("AC") component of the signal SP. The pulse wave signal $SM_1$ is supplied to the control device 28 via a second analog to digital (A/D) converter 30. The pulse wave signal $SM_1$ is representative of a pulse wave, i.e., oscillatory pressure wave produced from a brachial artery of the patient in synchronism with heartbeat of the patient and transmitted to the cuff 10 via the tissue positioned between the artery and the cuff 10. In the present embodiment, the cuff 10 serves as a pressing device for pressing the patient's upper arm 12 as a body portion of a living subject.

The control device 28 consists of a microcomputer which includes a central processing unit (CPU), a read only memory (ROM), a random access memory (RAM), and an input and output (I/O) port. The CPU processes supplied signals according to control programs stored in the ROM by utilizing a temporary-storage function of the RAM, and supplies drive signals to the selector valve 16 and the first air pump 18 through the I/O port and respective drive circuits (not shown) so as to regulate the cuff pressure P. In addition, the CPU of the control device 28 operates for determining a blood pressure (e.g., systolic and diastolic pressures) of the patient, based on variation of the amplitudes of pulses of the pulse wave signal $SM_1$ obtained while the cuff pressure P is slowly decreased. The control device 28 commands a display 32 including a cathode ray tube (CRT), to indicate the measured blood pressure values on the CRT. The control device 28 repeats this blood pressure measurement using the cuff 10, at predetermined intervals of time. In the present embodiment, the cuff 10, pressure sensor 14, selector valve 16, first air pump 18, static-pressure filter circuit 22, pulse-wave filter circuit 24, first and second A/D converters 26, 30, and control device 28 cooperate with each other to serve as blood pressure measuring means for measuring an actual or standard blood pressure of a subject by pressing a body portion of the subject with the cuff 10 as a pressing device.

As shown in FIG. 1, the present monitor system further includes a pulse wave detector probe 34. The probe 34 includes a container-like housing 36 which is detachably set on a body surface 38 of a wrist 42 of the patient with a pair of bands 40, 40 fastened around the wrist 42, such that the open end of the housing 36 contacts the body surface 38 of the wrist 42. In the present embodiment, the probe 34 is worn on one of two superior limbs of the patient different from the other superior limb on which the cuff 10 is worn.

A pulse wave sensor 46 is supported by the housing 36 via an elastic diaphragm 44, such that the pulse wave sensor 46 is displaceable relative to the housing 36, when the diaphragm 44 is inflated, so as to be advanceable out of the open end of the housing 36. The housing 36, diaphragm 44 and pulse wave sensor 46 cooperate with each other to define a pressure chamber 48, to which pressurized air is supplied from a second air pump 50 via a pressure-regulator valve 52. Thus, the pulse wave sensor 46 is pressed against the body surface 38 with a pressing force corresponding to the air pressure in the pressure chamber 48.

The pulse wave sensor 46 includes a plurality of semiconductor pressure-sensing elements (not shown) which are provided in one of opposite surfaces of a semiconductor substrate, such as a monocrystalline silicon, which one surface serves as a press surface 54 of the sensor 46. The pressure-sensing elements are arranged in an array at small intervals of distance in the press surface 54. The pulse wave sensor 46 is pressed on the body surface 38 of the wrist 42 such that the array of pressure-sensing elements cross over, or intersect, a radial artery 56 of the patient. Thus, each of the pressure-sensing elements of the pulse wave sensor 46 detects a pulse wave produced from the radial artery 56 in synchronism with heartbeat of the patient and transmitted to the body surface 38 or pressure surface 54, and generates a pulse-wave signal, $SM_2$, representative of the detected pulse wave. The pulse wave signals $SM_2$ from the pressure-sensing elements of the pulse wave sensor 46 are supplied to the control device 28 via a third analog to digital (A/D) converter 58. In the present embodiment, the radial artery 56 serves as an artery from which the pulse wave is detected, and the pulse wave detector probe 34, second air pump 50 and pressure-regulator valve 52 cooperate with each other to serve as pulse wave detecting means for detecting the pulse wave produced from the radial artery 56.

The control device 28 operates according to the control programs stored in the ROM, for supplying drive signals to the second air pump 50 and the pressure-regulator valve 52 via respective drive circuits (not shown), so as to regulate the air pressure in the pressure chamber 48. While slowly increasing the pressure in the chamber 48, the control device 28 collects the pulse wave signals $SM_2$ supplied from the individual pressure-sensing elements of the pulse wave sensor 46. Based on the thus collected pulse wave signals $SM_2$, the control device 28 determines an optimum air pressure (i.e., optimum pressing force) to be applied to the pulse wave sensor 46, by identifying an air pressure value in the chamber 48 at the time when the radial artery 56 is partially flattened under the pressing force of the pulse wave sensor 46. Since the manner of determination of the optimum pressing force is well known in the art, no more description is provided.

Based on the collected pulse wave signals $SM_2$, the control device 28 additionally selects an optimum pressure-sensing element located directly above the center of the radial artery 56, by identifying one of the pressure-sensing elements of the pulse wave sensor 46 which element provides a pulse wave signal $SM_2$ having the greatest amplitude of the amplitudes of all the pressure-sensing elements. Thus, the control device 28 controls the pressure regulator valve 52 so as to maintain the pressure chamber 48 at the determined optimum air pressure, and collects the pulse wave signal $SM_2$ from the optimum pressure-sensing element with the chamber 48 being maintained at the optimum air pressure. The control device 28 commands the display 32 to display a waveform of the pulse wave signal $SM_2$ from the optimum element. It is considered that, since the optimum element is located directly above the center of an artery 56, the pulse wave signal $SM_2$ from the optimum element is free of the influence due to the elastic, tensile force produced in the wall of the artery 56 and therefore accurately represents blood pressure variation inside the artery 56. That is, the waveform of the pulse wave signal $SM_2$ from the optimum pressure-sensing element accurately indicates variation in the blood pressure of the patient.

In addition, each time actual systolic and diastolic blood pressures are measured using the cuff 10, the control device 28 operates according to the control programs stored in the ROM, for determining a relationship between blood pressure and pulse wave magnitude ("BP-PW relationship), based on the measured systolic and diastolic blood pressure values and a maximum and a minimum magnitude (i.e., upper and lower peak magnitudes) of one pulse of the pulse wave signal $SM_2$ from the pulse wave sensor 46 (specifically, optimum pressure-sensing element). According to the thus determined BP-PW relationship, the control device 28 successively determines a systolic and a diastolic blood pressure of the patient, based on a maximum and a minimum magnitude of each of respective pulses of the pulse wave signal $SM_2$ after the BP-WP relationship has been determined, and commands the display 32 to indicate the determined blood pressure values one after another.

Furthermore, the control device 28 evaluates variation of the blood pressure of the patient, based on the maximum magnitudes and amplitudes of respective pulses of the pulse wave signal $SM_2$ after the BP-PW relationship has been determined. In the case where the maximum magnitudes and amplitudes of the pulse wave signal $SM_2$ satisfy predetermined conditions, the control device 28 evaluates the blood pressure variation as being large, and immediately effects a blood pressure measurement using the cuff 10 and updates the BP-PW relationship. On the other hand, in the case where the maximum magnitudes and amplitudes of the pulse wave signal $SM_2$ do not satisfy the predetermined conditions, the control device 28 deems the blood pressure variation as being small, and therefore permits the cuff-using blood pressure measurement and the BP-PW relationship updating to occur at the predetermined, considerably long interval. In the present embodiment, the control device 28 serves as (a) relationship determining means for determining a BP-PW relationship, and updates the relationship at intervals of time; (b) blood pressure monitoring means for continuously determining, according to the relationship, blood pressure values of the subject based on magnitudes of the pulse wave detected by the pulse wave detecting means; (d) blood pressure variation evaluating or determining means for determining a variation of the blood pressure of the subject; and (e) update-interval changing means for changing the interval of updating based on the blood pressure variation determined by the blood pressure variation evaluating or determining means.

Hereinafter, there will be described the operation of the present blood pressure monitoring system by reference to the flow charts f FIGS. 2 to 4.

Upon application of electric power to the present monitor system, the CPU of the control device 28 initializes the present system by, for example, clearing the contents of a flag, F, (described later). Subsequently, the CPU operates for effecting, in a parallel fashion, both the cuff-using blood pressure measuring routine of FIG. 2 and the blood pressure monitoring routine of FIG. 3.

Figure 2:
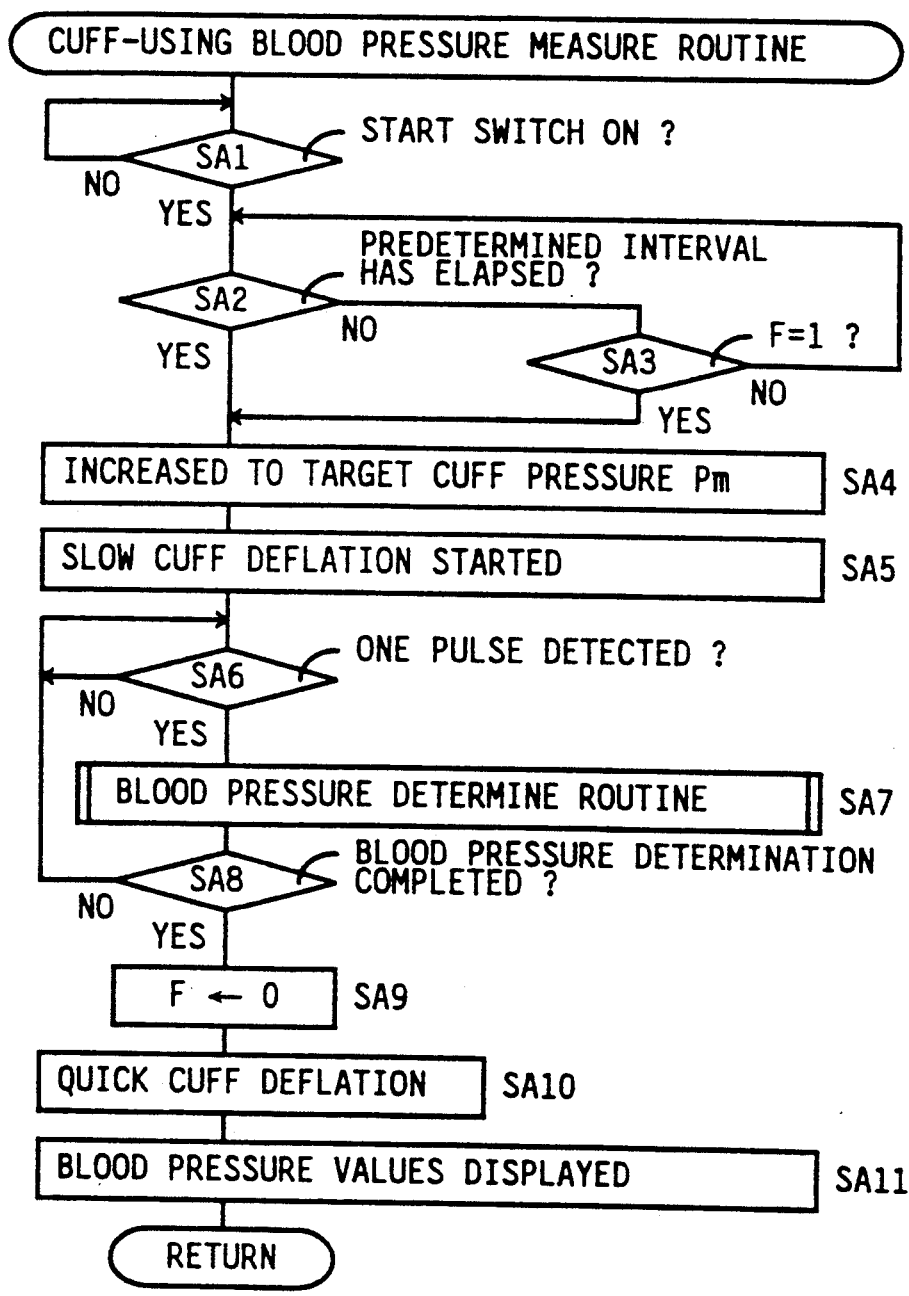
FIG. 2 is a flow chart representing a cuff-using blood pressure measure routine carried out by the blood pressure monitor system of FIG. 1.

The following explanation begins with the cuff-using blood pressure measuring routine of FIG. 2. In Step SA1 of this routine, the CPU judges whether or not a START switch (not shown) has been turned ON. If the judgement in Step SA1 is negative (NO), the control of the CPU waits for the START switch to be operated. If the judgement in Step SA1 is affirmative (YES), the control proceeds with Step SA2 in which the CPU judges whether or not a predetermined interval of time (e.g., twenty minutes) has elapsed. When a clock, register counts down to zero, the judgement in Step SA2 becomes affirmative. The present system is adapted such that the contents of the clock register is zero for the first or initial measurement cycle immediately after the START switch has been operated. In the first cycle, therefore, the judgement in SA2 is affirmative, and the control of the CPU goes to Step SA4. In Step SA4, the CPU places the selector valve 16 in the INFLATION position and actuates the first air pump 18, so as to increase the air pressure P in the cuff 10 up to a predetermined target value, Pm, (e.g., 180 mmHg) sufficiently higher than an estimated systolic (maximum) blood pressure of the patient. and then maintains the cuff pressure P at the target pressure Pm. Step SA4 is followed by Step SA5 to place the selector valve 16 in the SLOW-DEFLATION position, thereby causing the cuff pressure P to slowly be decreased.

Step SA5 is followed by Step SA6 to judge whether or not one pulse of the pulse wave signal $SM_1$ corresponding to one heartbeat of the patient has been supplied from the pulse-wave filter circuit 24. If the judgement in Step SA6 is negative, the CPU repeats Step SA6 until an affirmative judgement is made. If the judgement in Step SA6 becomes affirmative, the control of the CPU goes to Step SA7, i.e., blood pressure determination routine. In this step or routine, a systolic and a diastolic blood pressure are determined based on variation of the amplitudes of individual pulses of the pulse wave signal $SM_1$ obtained during the slow decreasing of the cuff pressure P. This is the well-known "oscillometric" blood pressure measuring method. In this step, a known algorithm is used for carrying out this method. Subsequently, the control of the CPU goes to Step SA8 to judge whether or not the blood pressure determination in Step SA7 has been completed. If the judgement in Step SA8 is negative, Steps SA6 and SA7 are repeated.

If the judgement in Step SA8 becomes affirmative after the blood pressure determination in Step SA7 has terminated, the control of the CPU goes to Step SA9 to reset the flag F to zero (F=0). Step SA9 is followed by Step SA10 to place the selector valve 16 in the QUICK-DEFLATION position, thereby deflating the cuff 10 and causing the cuff pressure P to quickly be decreased. Step SA10 is followed by Step SA11 in which the blood pressure values determined in Step SA7 are indicated on the display 32. Then, the control of the CPU goes back to Step SA1.

In the next or second measurement cycle, a negative judgement is made in Step SA2. Therefore, the control of the CPU proceeds with Step SA3 to judge whether or not the flag F is in the state of F=1. The flag F may be set to F=1 as a result of execution of the blood pressure monitoring routine of FIG. 3 (described later). The flag F is indicative of whether variation of the blood pressure of the patient is large or small; the state F=1 of the flag F indicates that the blood pressure variation is large. If the judgement in Step SA3 is negative, Steps SA2 and SA3 are repeated until an affirmative judgement is made in Step SA3. If the judgement in Step SA3 is affirmative, that is, if the blood pressure variation is large, the control of the CPU goes to Step SA4 and the following steps are performed to effect an actual or standard blood pressure measurement using the cuff 10, without any longer waiting for elapsing of the predetermined interval in Step SA2. Thus, the predetermined interval of standard blood pressure measurement is shortened when the blood pressure variation of the patient is identified as being large.

Figure 3:
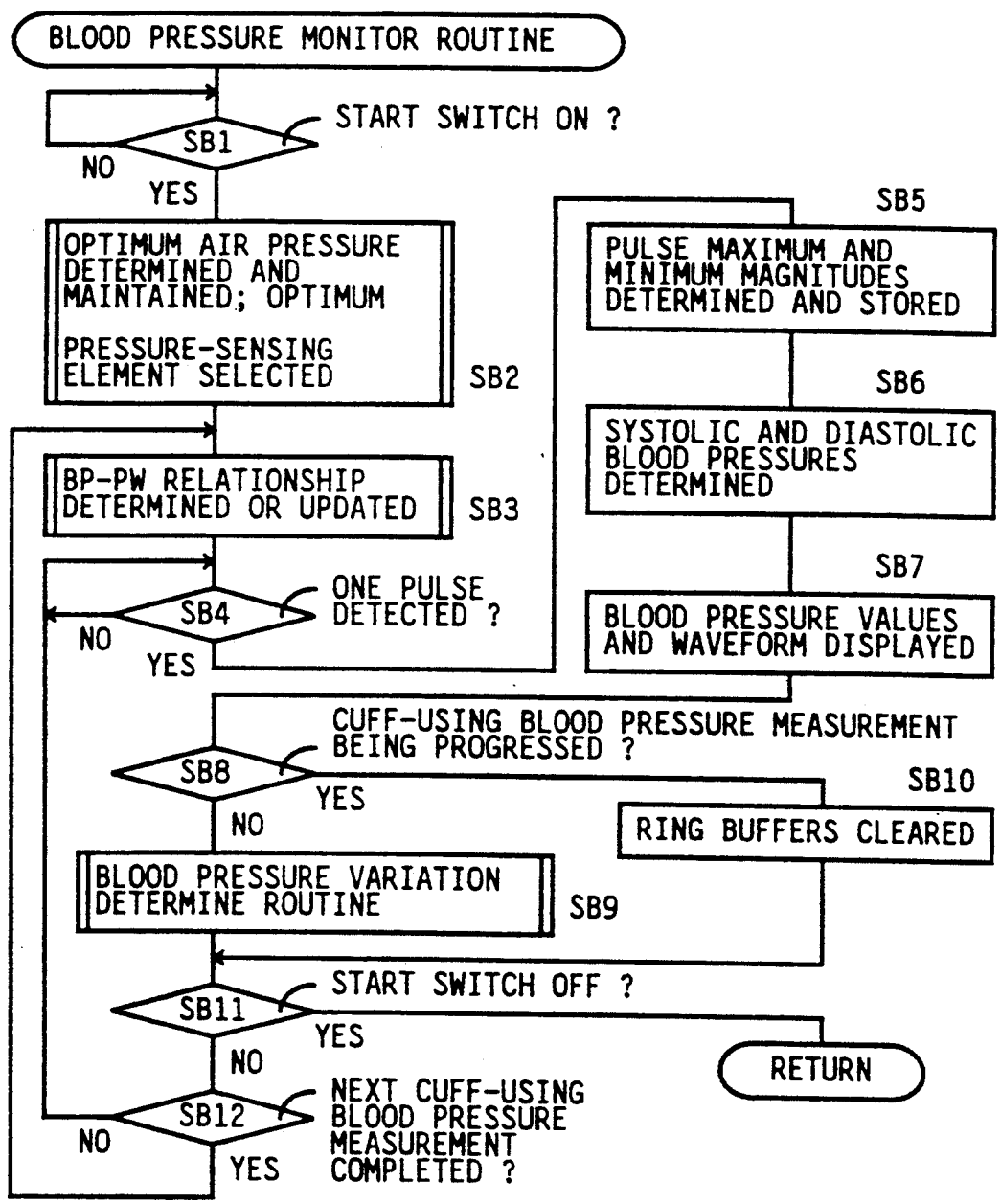
FIG. 3 is a flow chart representing the blood pressure monitoring routine carried out, in parallel with the routine of FIG. 2, by the blood pressure monitor system of FIG. 1.

Meanwhile, in the blood pressure monitoring routine of FIG. 3, first, in Step SB1, it is judged whether or not the aforementioned START switch has been turned ON. If the judgement in Step SB1 is negative, the control of the CPU repeats this step. If the judgement in this step becomes affirmative, the control goes to Step SB2. In this step, as described previously, the CPU determines the optimum air pressure (optimum pressing force) to be applied to the pulse wave sensor 46, based on the pulse wave signals SM2 supplied from the pressure-sensing elements of the pulse wave sensor 46 during the slow decreasing of the air pressure in the pressure chamber 48, and maintains the pressure in the chamber 48 at the determined optimum pressure. In addition, the CPU selects, from the pressure-sensing elements of the pulse wave sensor 46, the optimum pressure-sensing element which supplies a pulse wave signal SM2 having the greatest amplitude.

Step SB2 is followed by Step SB3 to determine a BP-PW relationship, based on the systolic and diastolic blood pressure values measured using the cuff 10, and a maximum and a minimum magnitude of a pulse of the pulse wave signal SM2 from the optimum pressure-sensing element. In each of the second and following cycles, a new BP-PW relationship is determined to replace the old one determined in the preceding cycle in this step. The manner of determination of the BP-PW relationship, is described in detail in U.S. Pat. No. 5,139,026 assigned to the Assignee of the present application, the disclosure of which is incorporated herein by reference.

Step SB3 is followed by Step SB4 to judge whether or not a pulse of the pulse wave signal SM2 corresponding to a heartbeat of the patient has been supplied from the optimum pressure-sensing element after the BP-PW relationship has been determined or updated in Step SB3. If the judgement in Step SB4 is negative, the CPU repeats this step. If an affirmative judgement is made in Step SB4, the control of the CPU proceeds with Step SB5 to determine the maximum and minimum magnitude of the pulse obtained in Step SB3, and store sets of data indicative of the determined pulse magnitudes in the RAM. In addition, a set of data indicative of the determined maximum magnitude is stored in a first ring buffer consisting of 150 storage areas each of which is capable of storing a set of pulse magnitude data. The first ring buffer is provided in the RAM of the control device 28.

Subsequently, the control of the CPU goes to Step SB6 to determine or estimate, according to the BP-PW relationship determined or updated in Step SB3, a systolic and a diastolic blood pressure of the patient, based on the maximum and minimum magnitudes of the pulse obtained in Step SB4. Step SB6 is followed by Step SB7 to indicate the determined blood pressure values and the waveform of the obtained pulse wave, on the display 32.

Step SB7 is followed by Step SB8 to judge whether or not a blood pressure measurement using the cuff 10 is being progressed in the routine of FIG. 2. If the judgement in Step SB8 is negative, the control of the CPU goes to Step SB9, i.e., blood pressure variation determination routine of FIG. 4, in which variation of the blood pressure of the patient is evaluated or determined based on the pulse wave signal SM2 from the optimum pressure-sensing element of the pulse wave sensor 46. Step SB9 is followed by Step SB11. On the other hand, if an affirmative judgement is made in Step SB8, the control goes to Step SB10 to clear the contents of both the aforementioned first ring buffer and a second ring buffer (described later). Step SB10 is followed by Step SB11.

In Step SB11, it is judged whether or not the START switch has been turned OFF. If the judgement in Step SB11 is affirmative, the control of the CPU goes back to Step SB1, and waits for another operation of the START switch. On the other hand, if the judgement in Step SB11 is negative, the control goes to Step SB12 to judge whether or not another blood pressure measurement using the cuff 10 has been effected and completed according to the algorithm of FIG. 2. So long as the judgement in Step SB12 continues to be negative, Steps SB4 to SB12 are repeated so that, each time a pulse of the pulse wave signal SM2 is supplied in Step SB4, a systolic and a diastolic blood pressure are determined based on a maximum and a minimum magnitude of the pulse by using the BP-PW relationship, and the determined blood pressure values are displayed together with the waveform of the pulse wave. Concurrently, the variation of the blood pressure of the patient is evaluated in Step SB9.

On the other hand, if the judgement in Step SB12 is affirmative, the control goes back to Step SB3 to update the BP-PW relationship by replacing the old one with a new one determined based on the systolic and diastolic blood pressures measured using the cuff 10 and a maximum and a minimum magnitude of a pulse of the pulse wave signal SM2 supplied just before, or after, the blood pressure measurement using the cuff 10 is completed. Thus, the BP-PW relationship is updated each time the cuff-using blood pressure measuring routine of FIG. 2 is effected to measure actual or standard systolic and diastolic blood pressure values. According to the periodically updated BP-PW relationship, the blood pressure of the patient is monitored by utilizing the pulse wave signal $SM_2$ supplied from the pulse wave sensor 46 (optimum pressure-sensing element).

Figure 4:
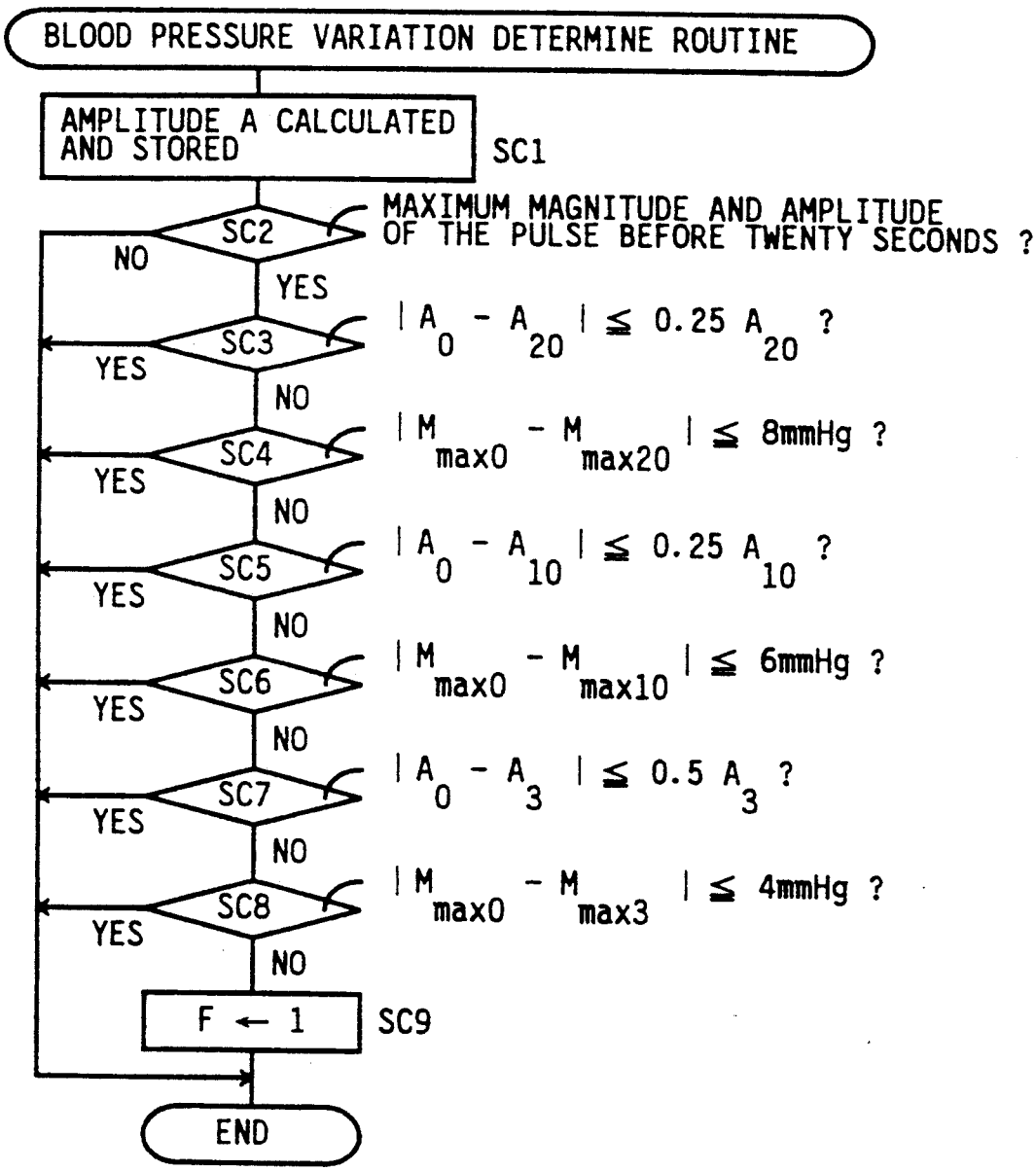
FIG. 4 is a flow chart representing a blood pressure variation determination routine as a part of the blood pressure monitor routine of FIG. 3.

In Step SB9, i.e., in the blood pressure variation determination routine of FIG. 4, first, in Step SC1, an amplitude, $A_0$, of the pulse of the signal $SM_2$ obtained in Step SB4 in the current cycle is calculated by subtracting from the maximum magnitude, $M_{max0}$, of the pulse the minimum magnitude, $M_{min0}$, of the pulse both of which are determined in Step SB5. A set of data indicative of the calculated amplitude $A_0$ is stored in a second ring buffer consisting of 150 storage areas each of which is capable of storing a set of pulse amplitude data.

Step SC1 is followed by Step SC2 to judge whether or not the first and second ring buffers hold a set of data indicative of a pulse maximum magnitude, $M_{max20}$, and a set of data indicative of a pulse amplitude, $A_{20}$, respectively, both of which relate to a pulse supplied twenty seconds before the current pulse is supplied. If the judgement in Step SC2 is affirmative, the control of the CPU goes to Step SC3 to judge whether or not the absolute value of the difference between the amplitudes $A_{20}$ and $A_0$ falls within a quarter (25%) of the amplitude $A_{20}$.

If the judgement in Step SC3 is negative, the control proceeds with Step SC4 to judge whether or not the absolute value of the difference between the maximum magnitudes $M_{max20}$ and $M_{max0}$ falls within 8 mmHg in terms of pressure (i.e., blood pressure). If the judgement in Step SC4 is negative, the control goes to Step SC5 to judge whether or not the absolute value of the difference between the amplitude $A_{10}$ of the pulse obtained ten seconds before and the amplitude $A_0$ of the current pulse falls within a quarter (25%) of the amplitude $A_{10}$. If the judgement in Step SC5 is negative, the control goes to Step SC6 to judge whether or not the absolute value of the difference between the maximum magnitude $M_{max10}$ of the pulse obtained ten seconds before and the maximum magnitude $M_{max0}$ of the current pulse falls within 6 mmHg.

If the judgement in Step SC6 is negative, the control goes to Step SC7 to judge whether or not the absolute value of the difference between the amplitude $A_3$ of the pulse obtained three seconds before and the amplitude $A_0$ of the current pulse falls within a half (50%) of the amplitude $A_3$. If the judgement in Step SC7 is negative, the control goes to Step SC8 to judge whether or not the absolute value of the difference between the maximum magnitude $M_{max3}$ of the pulse obtained three seconds before and the maximum magnitude $M_{max0}$ of the current pulse falls within 4 mmHg.

If the judgement in Step SC8 is negative, that is, if the judgement in Step SC2 is affirmative and, at the same time, if all the judgements in Steps SC3 to SC8 are negative, the control of the CPU goes to Step SC9 to set the flag F to F=1 indicating that the variation of the blood pressure of the patient is excessively large. Thus, the control exits this routine and goes to Step SB11 of FIG. 3.

On the other hand, if the judgement in Step SC2 is negative, or if any of the judgements in Steps SC3 to SC8 is affirmative, the control maintains the flag F at F=0 indicating that the blood pressure variation of the patient is sufficiently small. Similarly, the control exits this routine and goes to Step SB11.

In the case where the flag F is set to F=1 as a result of execution of the routine of FIG. 4, the judgement in Step SA3 of FIG. 2 turns affirmative, so that a blood pressure measurement using the cuff 10 is immediately initiated without any longer waiting for elapsing of the predetermined interval of time. Based on the thus measured actual or standard blood pressure values, the BP-PW relationship is updated in Step SB3. On the other hand, so long as the flag F continues to be at the state of F=0, the cuff-using blood pressure measurement and the BP-PW relationship updating are carried out at the predetermined interval.

In the present embodiment, the monitor system evaluates variation of the blood pressure of a living subject, based on the maximum magnitudes and amplitudes of respective pulses of the pulse wave signal $SM_2$ supplied from the pulse wave sensor 46 (or optimum pressure-sensing element), while the control device 28 monitors the blood pressure of the subject by using the currently effective BP-PW relationship. If the evaluation of the blood pressure variation shows that the variation is excessively large, the monitor system immediately carries out a blood pressure measurement using the cuff 10 and updates the BP-PW relationship based on the measured blood pressure, so that the monitor system continues to monitor the blood pressure of the subject by using the updated, accurate BP-PW relationship. Thus, even in the case where the blood pressure variation of the subject may be excessively large, the present monitoring system can continue to provide accurate blood pressure reading by utilizing the pulse wave signal $SM_2$ supplied from the pulse wave sensor 46.

In addition, while the blood pressure variation is sufficiently small or stable, the monitoring system carries out the cuff-using blood pressure measurement and the BP-PW relationship updating, at the predetermined, considerably long intervals. Thus, the present monitoring system advantageously reduces the patient's discomfort by lowering the frequency of pressing of patient's upper arm 12 with the inflatable cuff 10.

Hereinafter, there will be described other embodiments in accordance with the present invention.

Figure 5:
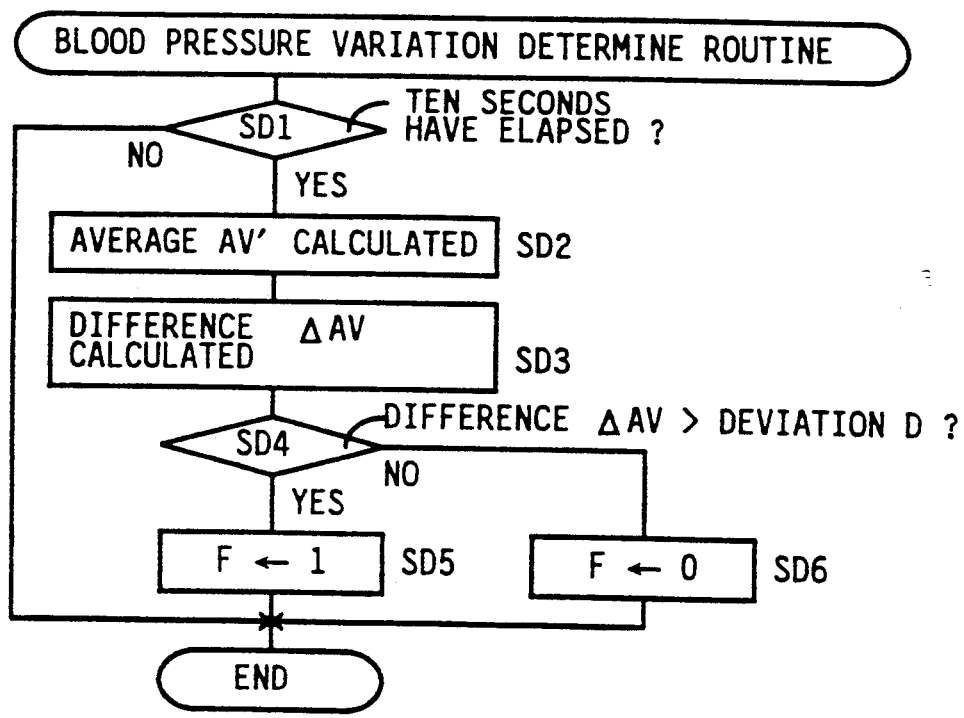
FIG. 5 is a flow chart representing another blood pressure variation determination routine which may be used i the blood pressure monitor system of FIG. 1.

FIG. 5 shows another blood pressure variation determination routine which may be used in Step SB9 of FIG. 3 in place of the routine of FIG. 4. For effecting the routine of FIG. 5, pulses of the pulse wave signal $SM_2$ are, in advance, collected and stored for ten seconds after the BP-PW relationship has been determined or updated, and the greatest maximum magnitude, MAX, and the smallest minimum magnitude, MIN, are selected from the collected pulses. In addition, are calculated an average, MID, of the magnitudes MAX and MIN, and an average, AV, of all the maximum and minimum magnitudes of the collected pulses except the magnitudes MAX, MIN. Then, the absolute value of the difference between the averages MID and AV is obtained as a deviation, D. The deviation D is indicative of a physiological blood pressure variation due to respiration of the patient.

Specifically, in Step SD1, it is judged whether or not every ten seconds (ten, twenty, thirty, seconds) have elapsed after the deviation D is determined. If the judgement in Step SD1 is negative, the control of the CPU exits this routine and goes to Step SB 11 of FIG. 3. Meanwhile, if an affirmative judgement is made in Step SD1, the control goes to Step SD2 to calculate, like the average AV, an average, AV', of all the maximum and minimum magnitudes of the pulses obtained in the ten seconds except the greatest pulse maximum magnitude and the smallest pulse minimum magnitude. Step SD2 is followed by Step SD3 to calculate the absolute value, ΔAV, of the difference between the time-wise adjacent two averages, that is, the average AV' of the current ten-second period and the average AV' of the preceding ten-second period (only for the first or initial cycle, the latter is the average AV). Subsequently, the control goes to Step SD4 to judge whether or not the difference ΔAV is greater than the deviation D. If the judgement in Step SD4 is affirmative, the CPU sets the flag F to F=1 in Step SD5. If otherwise, the CPU sets the flag F to F=0 in Step SD6. Step SD6 may be omitted. In this case, the difference ΔAV is used as a variation of the blood pressure of the patient.

Figure 6:
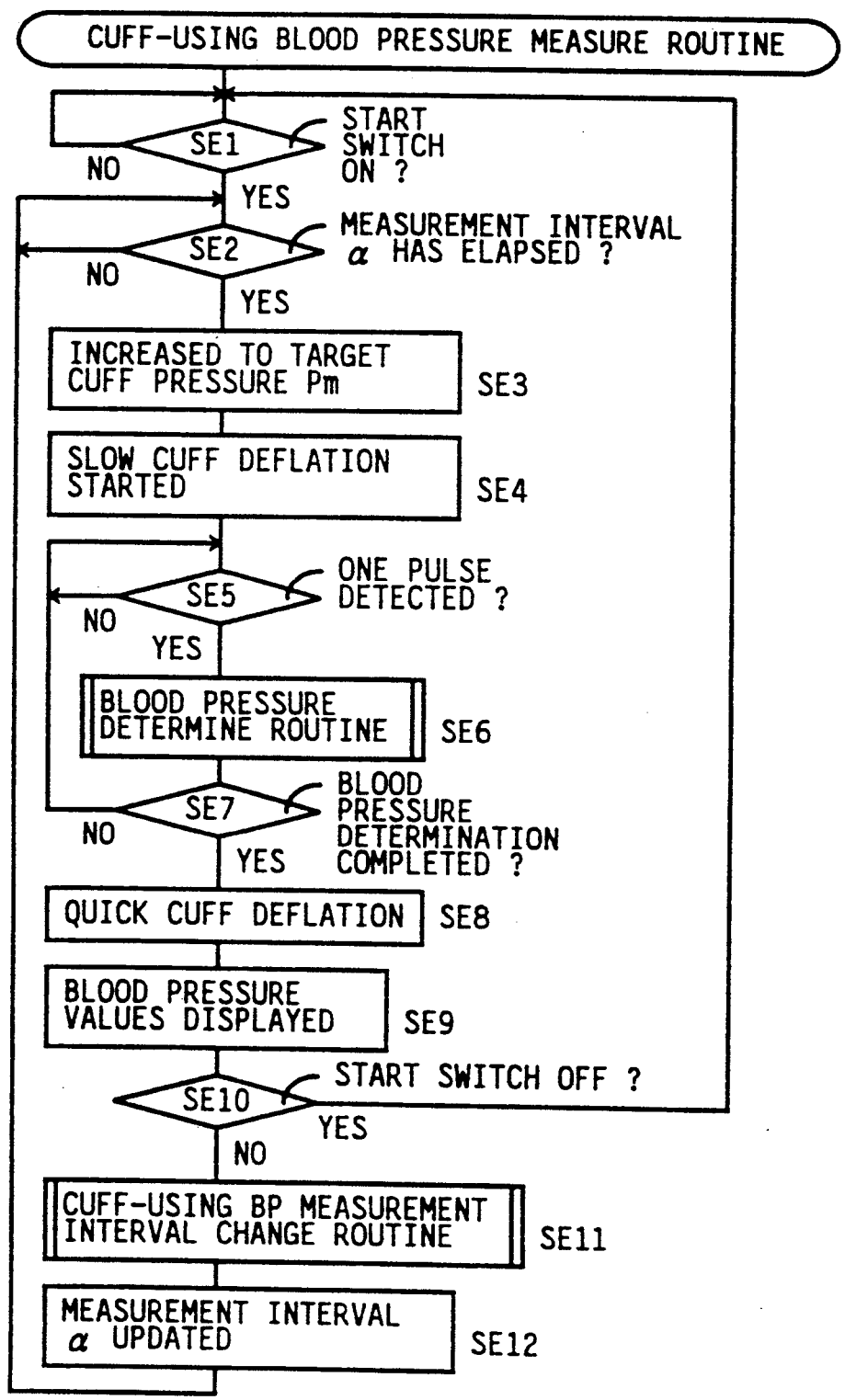
FIG. 6 is a flow chart representing another cuff-using blood pressure measurement routine which may be used in the blood pressure monitor system of FIG. 1.

FIG. 6 shows another cuff-using blood pressure measuring routine which may be used in place of the routine of FIG. 2. In the routine of FIG. 6, the cuff-using blood pressure measurement interval, i.e., BP-PW relationship updating interval is changed based on the blood pressure variation and other physiological indicators of the patient, each time a cuff-using blood pressure measurement is completed. The routine of FIG. 6 is different from the routine of FIG. 2 only with respect to Steps SE2 and SE10 to SE12, which will be described below.

Figure 7:
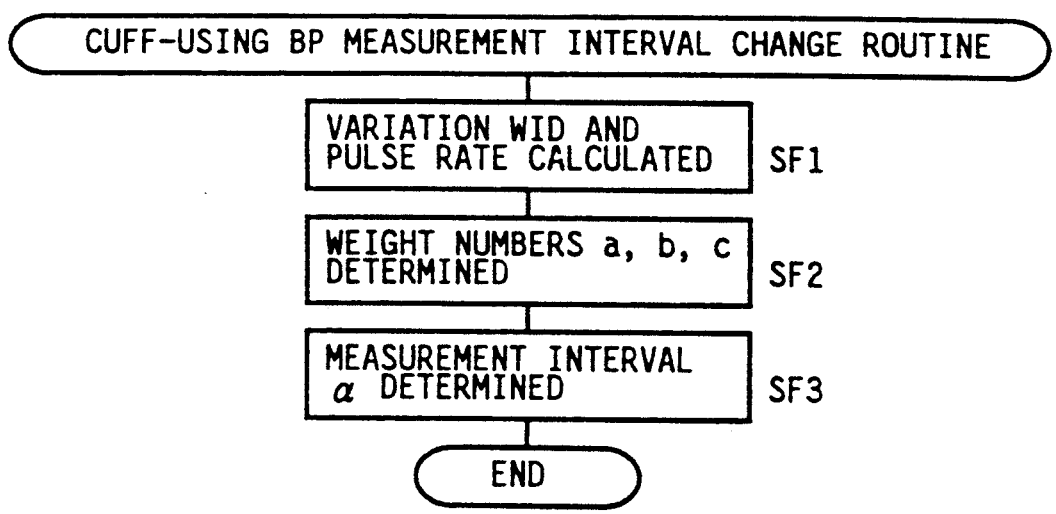
FIG. 7 is a flow chart representing a cuff-using BP (blood pressure) measurement interval change routine as a part of the cuff-using blood pressure measurement routine of FIG. 6.

In Step SE2, the CPU waits for elapsed of a time duration, α. In Step SE10, it is judged whether or not the START switch has been turned OFF. If the judgement in Step SE10 is affirmative, the control goes back to Step SE1 and waits. Meanwhile, if otherwise, the control goes to Step SE11, i.e., cuff-using BP (blood pressure) measurement interval determination routine of FIG. 7. In the routine of FIG. 7, first, in Step SF1, the CPU determines the absolute value, WID, of the difference between the greatest and smallest ones of the maximum magnitudes of the respective pulses of the signal $SM_2$ obtained during ten seconds after the BP-PW relationship is determined or updated in Step SB3 of FIG. 3. In addition, a pulse rate, R, (number of pulses per minute) of the patient is calculated based on the number of the pulses actually obtained during the ten seconds.

Step SF1 is followed by Step SF2 in which the CPU selects, from TABLE I, weighted values, a, b and c, which respectively correspond to the systolic blood pressure, SYS, obtained in Step SE6 in the current cycle, the aforementioned difference WID, and the pulse rate R. Step SF2 is followed by Step SF3 to calculate a time duration α by the following formula: α=180/(a+b+c). Thus, the CPU exits this routine and goes to Step SE12 of FIG. 6. In Step SE12, the CPU replaces the old time duration by the new one α determined in Step SF 3 of FIG. 7. Then, the control of the CPU goes back to Step SE2.

TABLE I

| PHYSIOLOGICAL INDICATORS | RANKS | WEIGHTED VALUES |
|---|---|---|
| DIFFERENCE WID (mmHg) | WID ≧ 20 | 60 |
| | 20 > WID ≧ 15 | 40 |
| | 15 > WID ≧ 10 | 27 |
| | 10 > WID ≧ 5 | 10 |
| | 5 > WID | 1 |
| BLOOD PRESSURE SYS (mmHg) | SYS ≧ 160 | 60 |
| | 160 > SYS ≧ 140 | 38 |
| | 140 > SYS ≧ 100 | 1 |

TABLE I-continued

| PHYSIOLOGICAL INDICATORS | RANKS | WEIGHTED VALUES |
|---|---|---|
| | 100 > SYS | 60 |
| PULSE RATE R | R ≧ 110 | 60 |
| | 110 > R ≧ 70 | 1 |
| | 70 > R | 60 |

The weighted values shown in Table I are determined so that the time duration α is shortened in concordance with the increased blood pressure variation (represented by the difference WID), and lengthened in concordance with the decreased blood pressure variation. In the present embodiment, Step SF1 of FIG. 7 and a portion of the control device 28 for effecting this step serve as blood pressure variation determining means, and Steps SF2 and SF3 and a portion of the control device 28 for effecting these steps serve as update-interval changing means for changing the time duration or update interval α. In this embodiment, Steps SB8 to SB10 are omitted from the routine of FIG. 3.

While the present invention has been described in its preferred embodiments, it is to be understood that the invention may otherwise be embodied.

For example, the blood pressure monitor system of FIG. 1 may be adapted to produce an alarm, or light a lamp, indicating that the variation of blood pressure of a subject is excessively large, when the system detects it.

While in the embodiment of FIGS. 1 to 4 the monitoring system evaluates the variation of blood pressure of a subject based on the maximum magnitudes and amplitudes of the pulse wave signal $SM_2$, the blood pressure variation may be evaluated based on the combination of the maximum and minimum magnitudes of the signal $SM_2$, as shown in the embodiment of FIG. 5, or the maximum magnitudes of the signal $SM_2$ as shown in the embodiment of FIG. 7. Otherwise, it is possible to evaluate the blood pressure variation by utilizing the maximum magnitude, minimum magnitude, average magnitude, or amplitude of the pulses of the signal $SM_2$, either in any appropriate combination thereof, or alone.

Although in the illustrated embodiments it is assumed that the cuff 10 and the pulse wave sensor 46 are worn on the different superior limbs of a subject, it is possible to set the two elements 10, 46 on the same and one superior limb. In this particular case, Step SB8 is effected . after Step SB3 and before Step SB4 in the blood pressure monitoring routine of FIG. 3.

While in the illustrated embodiments the cuff 10 is set on the upper arm 12 of the patient and the pulse wave detector probe 34 is set on the wrist 42 of the patient, it is possible that the cuff 10 be set on a thigh of the patient and the probe 34 be set on an ankle of the patient.

Although in the illustrated embodiments the pulse wave signal $SM_2$ from the pulse wave sensor 34 is used for monitoring the blood pressure of the patient, it is possible to use for the same purpose the pulse wave signal $SM_1$ supplied from the pulse wave filter circuit 24, by pressing the upper arm 12 with the cuff 12 at a considerably small pressure during each intermediate duration between time-wise adjacent blood pressure measurements using the cuff 10. In this case, the pulse wave detector probe 34 and its associated elements 50, 52, 58 are omitted.

While in the illustrated embodiments the cuff-using blood pressure measurement is effected by the "oscillometric" method using the pressure sensor 14, it is possible to carry out that measurement by the well-known "Korotkoff-sound" method in which a microphone is used for detecting appearance and disappearance of Korotkoff sounds from an artery when the cuff pressure P is decreased or increased.

It is to be understood that the present invention may be embodied with other changes, improvements and modifications that may occur to those skilled in the art without departing from the scope and spirit of the invention defined in the appended claims.

What is claimed is:

1. A blood pressure monitor system, comprising:

pulse wave detecting means for detecting a series of pulses of a pressure pulse wave produced from a single artery of a living subject in synchronism with heartbeat of said subject, said detecting means including a plurality of pressure sensing elements which are adapted to contact a body surface of said subject directly above said artery, said artery extending in a blood flow direction and said sensing elements extending in a direction crossing said blood flow direction;

pressing means for pressing said pulse wave detecting means against said artery through said body surface to partially flatten a wall of said artery, so that at least one of said pressure sensing elements detects said pulse wave through the flattened wall of said artery;

blood pressure measuring means including an inflatable cuff, for measuring a blood pressure of said subject by pressing a body portion of said subject with said cuff;

relationship determining means for determining a relationship between blood pressure and pulse wave magnitude, based on a pulse wave magnitude detected by said at least one pressure sensing element of said pulse wave detecting means through said flattened wall of said artery and a blood pressure value measured by said blood pressure measuring means, said relationship determining means determining a linear function equation defining said relationship, said linear function equation being expressed as $P = a \cdot M + b$ wherein P is blood pressure, M is pulse wave magnitude, and a, b are constants;

blood pressure monitor means for continuously determining, according to said relationship, blood pressure values of said subject based on magnitudes of the pulse wave detected by said at least one pressure sensing element of said pulse wave detecting means through said flattened wall of said artery;

said relationship determining means updating said relationship at intervals of time, based on blood pressure values measured by said blood pressure measuring means;

blood pressure variation determining means for determining a variation of the blood pressure of said subject, based on at least two of said magnitudes of the pulse wave detected by said at least one pressure sensing element of said pulse wave detecting means; and update-interval changing means for changing said interval of updating based on the blood pressure variation determined by said blood pressure variation determining means.

2. The blood pressure monitor system as set forth in claim 1, wherein said blood pressure variation determining means determines, as said variation of the blood pressure of said subject, an absolute value of a difference between a maximum magnitude of each of said pulses of the pulse wave detected by said pulse wave detecting means and a maximum magnitude of a prior one of said pulses detected a predetermined time before said each pulse.

3. The blood pressure monitor system as set forth in claim 2, wherein said update-interval changing means changes said interval of updating, by commanding said blood pressure measuring means and said relationship determining means to update said relationship, when said variation of the blood pressure is greater than a predetermined reference value.

4. The blood pressure monitor system as set forth in claim 1, wherein said blood pressure variation determining means determines, as a first variation of the blood pressure of said subject, an absolute value of a difference between a maximum magnitude of each of said pulses of the pulse wave detected by said pulse wave detecting means and a maximum magnitude of a first prior one of said pulses detected a first predetermined time before said each pulse, and determines, as a second variation of the blood pressure, an absolute value of a difference between said maximum magnitude of said each pulse and a maximum magnitude of a second prior one of said pulses detected a second predetermined time before said each pulse, said second predetermined time being shorter than said first predetermined time, said update-interval changing means changing said interval of updating, by commanding said blood pressure measuring means and said relationship determining means to update said relationship, when said first and second variations of the blood pressure are greater than a first and a second predetermined reference value, respectively.

5. The blood pressure monitor system as set forth in claim 1, wherein said blood pressure variation determining means calculates an amplitude of each of said pulses of the pulse wave detected by said pulse wave detecting means, by subtracting a minimum magnitude of said each pulse from a maximum magnitude of said each pulse, and determines as said variation of the blood pressure of said subject an absolute value of a difference between said amplitude of said each pulse and an amplitude of a prior one of said pulses detected a predetermined time before said each pulse.

6. The blood pressure monitor system as set forth in claim 5, wherein said update-interval changing means changes said interval of updating, by commanding said blood pressure measuring means and said relationship determining means to update said relationship, when said variation of the blood pressure is greater than a reference value.

7. The blood pressure monitor system as set forth in claim 6, wherein said update-interval changing means determines said reference value based on said amplitude of said prior one pulse.

8. The blood pressure monitor system as set forth in claim 1, wherein said blood pressure variation determining means determines, as a first variation of the blood pressure of said subject, an absolute value of a difference between an amplitude of each of said pulses of the pulse wave detected by said pulse wave detecting means and an amplitude of a first prior one of said pulses detected a first predetermined time before said each pulse, and determines, as a second variation of the blood pressure, an absolute value of a difference between said amplitude of said each pulse and an amplitude of a second prior one of said pulses detected a second predetermined time before said each pulse, said second predetermined time being shorter than said first predetermined time, said update-interval changing means determining a first reference value based on said amplitude of said first prior one pulse, and a second reference value based on said amplitude of said second prior one pulse, said update-interval changing means changing said interval of updating, by commanding said blood pressure measuring means and said relationship determining means to update said relationship, when said first and second variations of the blood pressure are greater than said first and second reference values, respectively.

9. The blood pressure monitor system as set forth in claim 1, wherein said blood pressure variation determining means determines (a) as a first variation of the blood pressure of said subject an absolute value of a difference between a maximum magnitude of each of said pulses of the pulse wave detected by said pulse wave detecting means and a maximum magnitude of a first prior one of said pulses detected a first predetermined time before said each pulse, determines (b) as a second variation of the blood pressure an absolute value of a difference between said maximum magnitude of said each pulse and a maximum magnitude of a second prior one of said pulses detected a second predetermined time before said each pulse, said second predetermined time being shorter than said first predetermined time, determines (c) as a third variation of the blood pressure an absolute value of a difference between an amplitude of said each pulse and an amplitude of said first prior one pulse, and determines (d) as a fourth variation of the blood pressure an absolute value of a difference between said amplitude of said each pulse and an amplitude of said second prior one pulse, said update-interval changing means changing said interval of updating, by commanding said blood pressure measuring means and said relationship determining means to update said relationship, when said first, second, third, and fourth variations of the blood pressure are greater than a first and a second predetermined reference value and a third and a fourth reference value, respectively, said update-interval changing means determining said third reference value based on said amplitude of said first prior one pulse, and said fourth reference value based n said amplitude of said second prior one pulse.

10. The blood pressure monitor system as set forth in claim 1, wherein said blood pressure variation determining means selects, rom the pulses of the pulse wave detected by said pulse wave detecting means during a first predetermined time duration after said relationship is updated by said relationship determining means, a pulse having a greatest maximum magnitude, MAX, of maximum magnitudes of said pulses and a pulse having a smallest minimum magnitude, MIN, of minimum magnitudes of said pulses, calculates an average, MID, of said magnitudes MAX, MIN, calculates an average, AV, of the maximum and minimum magnitudes of said pulses except said magnitudes MAX, MIN, determines as a deviation, D, an absolute value of a difference between said averages MID, AV, and successively calculates an average, AV', of maximum and minimum magnitudes of the pulses of the pulses wave detected during every second predetermined time duration after said deviation D is determined, said blood pressure variation determining means determining, as said variation of the blood pressure of said subject, an absolute value of a difference between time-wise adjacent two of said average AV and the averages AV'.

11. The blood pressure monitor system as set forth in claim 10, wherein said update-interval changing means changes said interval of updating, by commanding said blood pressure measuring means and said relationship determining means to update said relationship, when said variation of the blood pressure is greater than said deviation D.

12. The blood pressure monitor system as set forth in claim 1, wherein said blood pressure variation determining means selects, from the pulses of the pulse wave detected by said pulse wave detecting means during a predetermined time duration after said relationship is updated by said relationship determining means, pulse having a greatest maximum magnitude of maximum magnitudes of said pulses and a pulse having a smallest maximum magnitude of said maximum magnitudes, and determines, as said variation of the blood pressure of said subject, an absolute value of a difference between said greatest and smallest maximum magnitudes.

13. The blood pressure monitor system as set forth in claim 12, wherein said update-interval changing means determines a first weighted value, a, corresponding to said variation of the blood pressure, and a second weighted value, b, corresponding to a value of a physiological indicator indicative of a physical condition of said subject different from the maximum magnitude of the pulses of the pulse wave, and changes said interval of updating based on said weighted values a, b.

14. The blood pressure monitor system as set forth in claim 13, wherein said update-interval changing means changes said interval of updating to a value obtained by dividing a reference value by a sum of said weighted values a, b.

15. The blood pressure monitor system as set forth in claim 1, wherein said blood pressure variation determining means determines said variation of the blood pressure of said subject, by utilizing at least one physiological indicator selected from maximum magnitude, minimum magnitude, average magnitude, and amplitude of the pulses of the pulse wave.

16. The blood pressure monitor system as set forth in claim 1, further comprising display means for displaying a waveform of said pulse wave detected by said pulse wave detecting means, said blood pressure value measured by said blood pressure measuring means, and said blood pressure values determined by said blood pressure monitor means.

17. A blood pressure monitor method, comprising the steps of:

pressing a pulse wave sensor including a plurality of pressure sensing elements, against a single artery of a living subject through a body surface of said subject, such that said pulse wave sensor partially flattens a wall of said artery and that said pressure sensing elements contact said body surface of said subject directly above said artery, said artery extending in a blood flow direction and said sensing elements extending in a direction crossing said blood flow direction, detecting, using at least one of said pressure sensing elements of said pulse wave sensor, a series of pulses of a pressure pulse wave produced from the flattened wall of said artery of said living subject in synchronism with a heartbeat of said subject, measuring, using an inflatable cuff, a blood pressure of said subject by pressing a body portion of said subject with said cuff, determining a relationship between blood pressure and pulse wave magnitude, based on a pulse wave magnitude detected by said at least one pressure sensing element through said flattened wall of said artery and a blood pressure value measured using said cuff, such that said relationship is defined by a linear function equation which is expressed as $P = a \cdot M + b$ wherein P is blood pressure, M is pulse wave magnitude, and a, b are constants, continuously determining, according to said relationship, blood pressure values of said subject based on magnitudes of the pulse wave detected by said at least one pressure sensing element through said flattened wall of said artery, updating said relationship at intervals of time, based on blood pressure values measured using said cuff, determining a variation of the blood pressure of said subject, based on at least two of said magnitudes of the pulse wave detected by said at least one pressure sensing element, and changing said interval of updating based on the determined blood pressure variation.

18. A blood pressure monitor system, comprising:

pulse wave detecting means for detecting a series of pulses of a pressure pulse wave produced from a single artery of a living subject in synchronism with heartbeat of said subject, said detecting means including a plurality of pressure sensing elements which are adapted to contact a body surface of said subject directly above said artery, said artery extending in a blood flow direction and said sensing elements extending in a direction crossing said blood flow direction;

pressing means for pressing said pulse wave detecting means against said artery through said body surface to partially flatten a wall of said artery, so that at least one of said pressure sensing elements detects said pulse wave through the flattened wall of said artery;

blood pressure measuring means including an inflatable cuff, for measuring a blood pressure of said subject by pressing a body portion of said subject with said cuff;

relationship determining means for determining a relationship between blood pressure and pulse wave magnitude, based on a pulse wave magnitude detected by said at least one pressure sensing element of said pulse wave detecting means through said flattened wall of said artery and a blood pressure value measured by said blood pressure measuring means;

blood pressure monitor means for continuously determining, according to said relationship, blood pressure values of said subject based on magnitudes of the pulse wave detected by said at least one pressure sensing element of said pulse wave detecting means through said flattened wall of said artery;

said relationship determining means updating said relationship at intervals of time, based on blood pressure values measured by said blood pressure measuring means;

blood pressure variation determining means for determining a variation of the blood pressure of said subject, based on at least two of said magnitudes of the pulse wave detected by said at least one pressure sensing element of said pulse wave detecting means, said blood pressure variation determining means selecting, from the pulses of the pulse wave detected by said pulse wave detecting means during a first predetermined time duration after said relationship is updated by said relationship determining means, a pulse having a greatest maximum magnitude, MAX, of maximum magnitudes of said pulses and a pulse having a smallest minimum magnitude, MIN, of minimum magnitudes of said pulses, calculating an average, MID, of said greatest maximum and smallest minimum magnitudes MAX, MIN, calculating an average, AV, of the maximum and minimum magnitudes of said pulses except said magnitudes MAX, MIN, determining as a deviation, D, an absolute value of a difference between said averages MID, AV, and successively calculating an average, AV', of maximum and minimum magnitudes of the pulses of the pulse wave detected during every second predetermined time duration after said deviation D is determined, said blood pressure variation determining means determining, as said variation of the blood pressure of said subject, an absolute value of a difference between time-wise adjacent two of said average AV and the averages AV'; and update-interval changing means for changing said interval of updating based on the blood pressure variation determined by said blood pressure variation determining means.

19. The blood pressure monitor system as set forth in claim 18, wherein said update-interval changing means changes said interval of updating, by commanding said blood pressure measuring means and said relationship determining means to update said relationship, when said variation of the blood pressure is greater than said deviation D.

20. A blood pressure monitor system, comprising:

pulse wave detecting means for detecting a series of pulses of a pressure pulse wave produced from a single artery of a living subject in synchronism with heartbeat of said subject, said detecting means including a plurality of pressure sensing elements which are adapted to contact a body surface of said subject directly above said artery, said artery extending in a blood flow direction and said sensing elements extending in a direction crossing said blood flow direction;

pressing means for pressing said pulse wave detecting means against said artery through said body surface to partially flatten a wall of said artery, so that at least one of said pressure sensing elements detects said pulse wave through the flattened wall of said artery;

blood pressure measuring means including an inflatable cuff, for measuring a blood pressure of said subject by pressing a body portion of said subject with said cuff;

relationship determining means for determining a relationship between blood pressure and pulse wave magnitude, based on a pulse wave magnitude detected by said at least one pressure sensing element of said pulse wave detecting means through said flattened wall of said artery and a blood pressure value measured by said blood pressure measuring means;

blood pressure monitor means for continuously determining, according to said relationship, blood pressure values of said subject based on magnitudes of the pulse wave detected by said at least one pressure sensing element of said pulse wave detecting means through said flattened wall of said artery;

said relationship determining means updating said relationship at intervals of time, based on blood pressure values measured by said blood pressure measuring means;

blood pressure variation determining means for determining a variation of the blood pressure of said subject, based on at least two of said magnitudes of the pulse wave detected by said at least one pressure sensing element of said pulse wave detecting means, said blood pressure variation determining means selecting, from the pulses of the pulse wave detected by said pulse wave detecting means during a predetermined time duration after said relationship is updated by said relationship determining means, a pulse having a greatest maximum magnitude out of maximum magnitudes of said pulses and a pulse having a smallest maximum magnitude out of said maximum magnitudes of said pulses, and determining, as said variation of the blood pressure of said subject, an absolute value of a difference between said greatest and smallest maximum magnitudes; and update-interval changing means for changing said interval of updating based on the blood pressure variation determined by said blood pressure variation determining means.

21. The blood pressure monitor system as set forth in claim 20, wherein said update-interval changing means determines a first weighted value, a, corresponding to said variation of the blood pressure, and a second weighted value, b, corresponding to a value of a physiological indicator indicative of a physical condition of said subject different from the maximum magnitude of the pulses of the pulse wave, and changes said interval of updating based on said weighted values a, b.

22. The blood pressure monitor system as set forth in claim 21, wherein said update-interval changing means changes said interval of updating to a value obtained by dividing a reference value by a sum of said weighted values a, b.

* * * * *